US 6,689,118 B2

(12) United States Patent
Alchas et al.

(10) Patent No.: US 6,689,118 B2
(45) Date of Patent: *Feb. 10, 2004

(54) METHOD OF INTRADERMALLY INJECTING SUBSTANCES

(75) Inventors: Paul G. Alchas, Wayne, NJ (US); Philippe Emile Fernand Laurent, Oullins (FR)

(73) Assignee: Becton Dickinson and Company, Franklin Lakes, NJ (US)

( * ) Notice: Subject to any disclaimer, the term of this patent is extended or adjusted under 35 U.S.C. 154(b) by 76 days.

This patent is subject to a terminal disclaimer.

(21) Appl. No.: 10/071,665

(22) Filed: Feb. 8, 2002

(65) Prior Publication Data

US 2002/0193778 A1 Dec. 19, 2002

Related U.S. Application Data

(63) Continuation of application No. 10/044,504, filed on Jan. 10, 2002, which is a continuation-in-part of application No. 09/835,243, filed on Apr. 13, 2001, now Pat. No. 6,569,143, which is a continuation-in-part of application No. 09/417,671, filed on Oct. 14, 1999, now Pat. No. 6,494,865.

(51) Int. Cl.⁷ ............................................. A61M 31/00
(52) U.S. Cl. ...................................... 604/506; 604/117
(58) Field of Search .............................. 604/506, 117, 604/187, 192, 198, 110, 164, 165, 162

(56) References Cited

U.S. PATENT DOCUMENTS

| 1,934,046 A | 11/1933 | Demarchi ..................... 128/215 |
| 2,876,770 A | 3/1959 | White ......................... 128/215 |
| 3,073,306 A | 1/1963 | Linder ........................ 128/215 |
| 3,400,715 A | 9/1968 | Pederson ..................... 128/215 |
| 3,890,971 A | 6/1975 | Leeson et al. ............... 128/218 |
| 4,060,073 A | 11/1977 | Collica et al. ............... 128/1.1 |
| 4,270,537 A | 6/1981 | Romaine ..................... 128/218 |
| 4,373,526 A | 2/1983 | King ........................... 604/117 |
| 4,583,978 A | 4/1986 | Porat et al. .................. 604/208 |
| 4,596,556 A | 6/1986 | Morrow et al. ............... 604/70 |
| 4,769,003 A | 9/1988 | Stamler ....................... 604/39 |
| 4,790,824 A | 12/1988 | Morrow et al. ............. 604/143 |

(List continued on next page.)

FOREIGN PATENT DOCUMENTS

| EP | 0279583 B1 | 10/1993 |
| EP | 0 904 790 A2 | 3/1999 |
| EP | 1066848 | 1/2001 |

(List continued on next page.)

OTHER PUBLICATIONS

International Search Report dated Dec. 20, 2001 for International Appln No. PCT/US01/12251.
International Search Report dated Dec. 20, 2001 for International Appln No. PCT/US01/12447.

(List continued on next page.)

*Primary Examiner*—Manuel Mendez
(74) *Attorney, Agent, or Firm*—David M. Fortunato

(57) ABSTRACT

A method of making an intradermal injection using a drug delivery device containing the substance to be injected. A device for practicing the method includes a needle cannula having a forward tip and a limiter portion having a skin engaging surface surrounding the needle cannula. The needle cannula is in fluid communication with the substance and the tip of the needle cannula extends beyond the skin engaging surface a distance equal to approximately 0.5 mm to 3.0 mm. The needle cannula includes a fixed angle of orientation relative to the plane of the skin engaging surface. The skin engaging surface limits penetration of the needle tip into the skin so that the substance can be expelled through the needle tip into the dermis layer. Preferably, the fixed angle of orientation of the needle cannula is generally perpendicular relative to the skin surface, and the skin engaging surface is generally flat.

57 Claims, 5 Drawing Sheets

U.S. PATENT DOCUMENTS

| | | | |
|---|---|---|---|
| 4,883,573 A | 11/1989 | Voss et al. | |
| 4,886,499 A | 12/1989 | Cirelli et al. | 604/131 |
| 4,898,588 A | 2/1990 | Roberts | 604/187 |
| 4,940,460 A | 7/1990 | Casey, I. et al. | 604/143 |
| 4,941,880 A | 7/1990 | Burns | 604/143 |
| 4,955,871 A | 9/1990 | Thomas | |
| 4,978,344 A | 12/1990 | Dombrowski et al. | 604/198 |
| 5,015,235 A | 5/1991 | Crossman | 604/117 |
| 5,064,413 A | 11/1991 | McKinnon et al. | 604/70 |
| 5,071,353 A | 12/1991 | van der Wal | 434/262 |
| 5,137,516 A | 8/1992 | Rand et al. | 604/136 |
| 5,141,496 A | 8/1992 | Dalto et al. | 604/117 |
| 5,190,521 A | 3/1993 | Hubbard et al. | 604/51 |
| 5,222,949 A | 6/1993 | Kaldany | |
| 5,312,335 A | 5/1994 | McKinnon et al. | 604/72 |
| 5,331,954 A | 7/1994 | Rex et al. | 128/200.22 |
| 5,334,144 A | 8/1994 | Alchas et al. | 604/68 |
| 5,339,163 A | 8/1994 | Homma et al. | 348/229 |
| 5,368,578 A | 11/1994 | Covington et al. | 604/232 |
| 5,383,851 A | 1/1995 | McKinnon, Jr. et al. | 604/68 |
| 5,417,662 A | 5/1995 | Hjertman et al. | 604/117 |
| 5,431,155 A | 7/1995 | Marelli | 128/200.14 |
| 5,437,647 A | 8/1995 | Firth et al. | 604/110 |
| 5,466,220 A | 11/1995 | Brenneman | 604/87 |
| 5,480,381 A | 1/1996 | Weston | 604/68 |
| 5,496,286 A | 3/1996 | Stiehl et al. | 604/232 |
| 5,503,627 A | 4/1996 | McKinnon et al. | 604/72 |
| 5,514,107 A | 5/1996 | Haber et al. | 604/197 |
| 5,520,639 A | 5/1996 | Peterson et al. | 604/68 |
| 5,527,288 A | 6/1996 | Gross et al. | 604/140 |
| 5,569,189 A | 10/1996 | Parsons | 604/68 |
| 5,578,014 A | 11/1996 | Erez et al. | 604/192 |
| 5,582,598 A | 12/1996 | Chanoch | 604/208 |
| 5,599,302 A | 2/1997 | Lilley et al. | 604/68 |
| 5,649,912 A | 7/1997 | Peterson | 604/187 |
| 5,665,071 A | 9/1997 | Wyrick | 604/134 |
| 5,702,362 A | 12/1997 | Herold et al. | 604/58 |
| 5,704,911 A | 1/1998 | Parsons | 604/72 |
| 5,779,677 A | 7/1998 | Frezza | 604/134 |
| 5,873,856 A | 2/1999 | Hjertman et al. | 604/117 |
| 5,879,327 A | 3/1999 | Moreau De Farges et al. | 604/68 |
| 5,891,085 A | 4/1999 | Lilley et al. | 604/68 |
| 5,893,397 A | 4/1999 | Peterson et al. | 141/27 |
| 5,921,963 A | 7/1999 | Erez et al. | 604/192 |
| 5,957,897 A | 9/1999 | Jeffrey | 604/223 |
| 5,961,495 A | 10/1999 | Walters et al. | 604/208 |
| 5,993,412 A | 11/1999 | Deily et al. | 604/68 |
| 6,001,089 A | 12/1999 | Burroughs et al. | 604/506 |
| 6,004,299 A | 12/1999 | Arai et al. | 604/218 |
| 6,036,675 A | 3/2000 | Thorne et al. | 604/232 |
| 6,053,893 A | 4/2000 | Bucher | 604/131 |
| 6,083,197 A | 7/2000 | Umbaugh | 604/68 |
| 6,090,077 A | 7/2000 | Shaw | 604/195 |
| 6,090,080 A | 7/2000 | Jost et al. | 604/207 |
| 6,090,082 A | 7/2000 | King et al. | 604/234 |
| 6,093,170 A | 7/2000 | Hsu et al. | 604/110 |
| 6,112,743 A | 9/2000 | Denton | 128/200.14 |
| 6,200,291 B1 | 3/2001 | Di Pietro | 604/117 |
| 6,210,369 B1 | 4/2001 | Wilmot et al. | 604/157 |
| 6,569,143 B2 * | 5/2003 | Alchas et al. | 604/506 |

FOREIGN PATENT DOCUMENTS

| | | |
|---|---|---|
| EP | 1092444 | 4/2001 |
| FR | 2612 401 A1 | 9/1988 |
| GB | 725024 | 3/1955 |
| GB | 735538 | 8/1955 |
| JP | 2000-37456 | 2/2000 |
| WO | 9309826 | 5/1993 |
| WO | WO 95/01198 | 1/1995 |
| WO | WO9713537 | 4/1997 |
| WO | WO9737705 | 10/1997 |
| WO | 9925402 | 5/1999 |
| WO | WO 99/27986 | 6/1999 |
| WO | WO 99/34850 | 7/1999 |
| WO | 9937345 | 7/1999 |
| WO | 0056384 | 9/2000 |

OTHER PUBLICATIONS

International Search Report dated Dec. 20, 2001 for International Appln No. PCT/US01/12248.

*Purified Influenza Vaccine: Clinical and Serologic Responses to Varying Doses and Different Routes of Inunnunization,* by C.A. Phillips, B.R. Forsyth, W.A. Christmas, D.W. Gump, E.B. Whorton, I. Rogers, and A. Rudin, from the Department of Medicine and Community Medicine, University of Vermont College of Medicine, Burlington, Vermont.

*Polyvalent Influenza Vaccine: Comparison of Jet Injection with Intradermal and Subcutaneous Syringe Methods of Administration,* authored by Mervin L. Clark. Herbert Reinhardt, M. Clinton Miller, III and Ray Wilson, Oklahoma City, Oklahoma.

*Experimental Comparison of Intradermal and Subcutaneous Vaccination with Influenza Vaccine,* from the American Journal of Medical Technology, vol. 31, Nov.–Dec. 1965, No.6.

*Intradermal Influenza Immununization, Experience with Hong Kong Vaccine,* from the American Review of Respiratory Disease, vol. 103, 1971.

*Efficacy of Adsorbed Trivalent Split Influenza Vaccine Administered by Intradermal Route,* by I, Th Niculescu, Eugenia Zilisteanu, V. Alexandrescu, Mihaela Matepiuc, Ligia Cretescu, N. Ionescu, G. Molnar, R. Racasan and Adina Mogos, received for publication Dec. 4, 1980, from Arch Roum. Path. Exp. Microbiol., T. 40, No. 1, pp. 67–70, Jan.–Mar., 1981.

*Efficacy of Intradermally Administered A2 Hong Kong Vaccine,* from Jama, from JAMA, Jul. 6, 1970, vol. 213, No. 1.

*Comparison of Responses to Influenza, A–New Jersey/76–A/Victoria/75 Virus Vaccine Administered Intradermally or Subcutaneously to Adults with Chronic Respiratory Disease,* authored by F. Alexander Herbert, R. P. Bryce Larke, and Edythe L. Markstad, from the Journal of Infectious Diseases, vol. 140, No. 2, Aug. 1979.

*A Comparison of the Intradermal and Subcutaneous Routes of Influenza Vaccination with A/New Jersey/76 (Swine Flu) and A/Victoria/75: Report of a Study and Review of the Literature,* by William Halperin, MD, MPH, William I. Weiss, MD Ronald Altman, MD, MPH, Michael A. Diamond MD, Kenneth J. Black, BA, Alfred W. Iaci, BBA, MS, Henry C. Black, DVM and Martin Goldfield, MD, from the ALPHA Dec. 1979, vol. 69, NO. 12.

*Effect of Dosage and Route of Inoculation Upon Antigenicity of Inactivated Influenza Virus Vaccine (Hong Kong Strain) in Man,* from Bull. Org. mond. Santé Bull. Wld Hlth Org. 1969, 41, 507–516.

*Comparative Analysis of Six European Influenza Vaccines,* from Eur. J. Clin. Microbiol. Infect. Dis. 1996, 15:121–127.

*Morphological and Biochemical Characterization of Influenza Vaccines Commercially Available in the United Kingdom,* by F. Renfrey and A. Watts, from Vaccine 1994, vol. 12, No. 8.

*Influenza Immununization Policies and Practices in Japan*, from the Jouranl of Infectious Diseases, vol. 141, No. 2, Feb. 1980.

*Clinical Immununogenicity and Tolerance Studies of Liquid Vaccines Delivered by Jet–Injector and a New Single–Use Cartridge (Imule®): Comparison with Standard Syringe Injection*, authored by Isabelle Parent du Chatelet, Jean Lang, Martin Schlumberger, Emmanuel Vidor, Georges Soula, Alain Gene, Steven M. Standaert, Pierre Saliou and Imule® Investigators Group, Vaccine 1997, vol. 15, No. 4.

Abstract: *Does a Needleless Injection System Reduce Anxiety in Children Receiving Intramuscular Injections?*, by Polillio AM, Kiley J, from the Pediatric Primary Care Clinic,Boston City Hospital, MA, USA. Pediatr. Nurs. 1997, Jan.–Feb.; 23(1):46–9.

Abstract: *Intradermal Administration of Viral Vaccines*, by Nagafuchi S., Kashiwagi S, Imayama S, Hayashi J, Niho Y, from Rev. Med. Virol. Apr. 1998; 8(2):97–111.

Abstract: *Letter: Intradermal Influenza Vaccination* by Payler DK, Skirrow MB, Br Med J Jun. 29, 1974; 2(921);727.

Intradermal Influenza Vaccination; British Medical Journal, Jun. 29, 1974.

Smith Kline Beecham Meeting Agenda.

Article: Dermal Immune System by Brian J. Nickoloff, MD, Phd.

Article: Trials of Intradermal Hepatitis B Vaccines in Gambian Children by Whittle, Lam, Ryder.

Article: Injection Technique Intradermal.

Article: The Dendritic Cell System and Its Role in Immunogenicity by Ralph Steinman.

Article: Intradermal Gene Immunization: The Possible Role of DNA Uptake in the Induction of Cellular Immunity to Viruses by: Eyal Raz et al.

Article: Clinical Do's & Don'ts—Giving Intradermal Injection by Edwina Mcconnell, RN, PhD.

Article: Monographs of the Physiological Society No. 12: Substances Producing Pain and Itch by C. A. Keele and D. Armstrong Pub: The Williams & Wilkins Company (1964).

\* cited by examiner

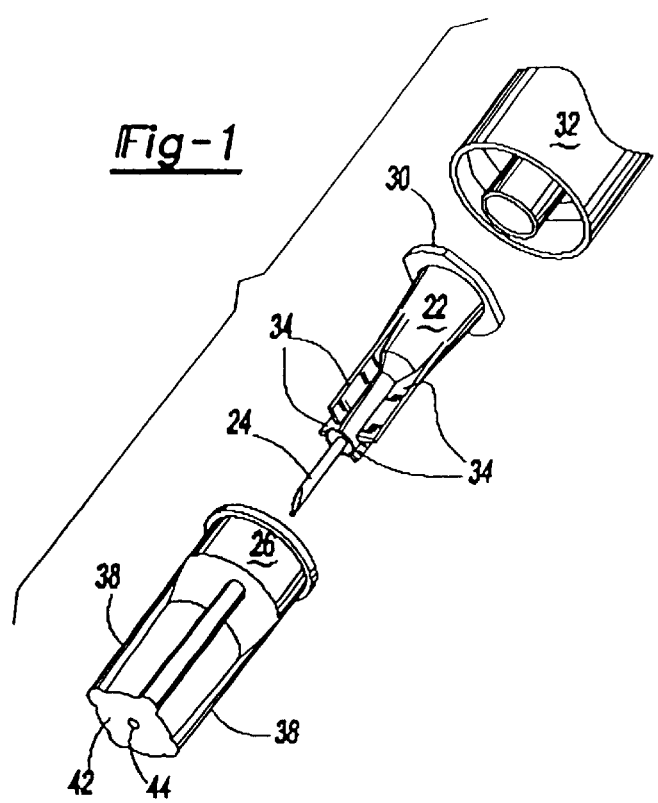
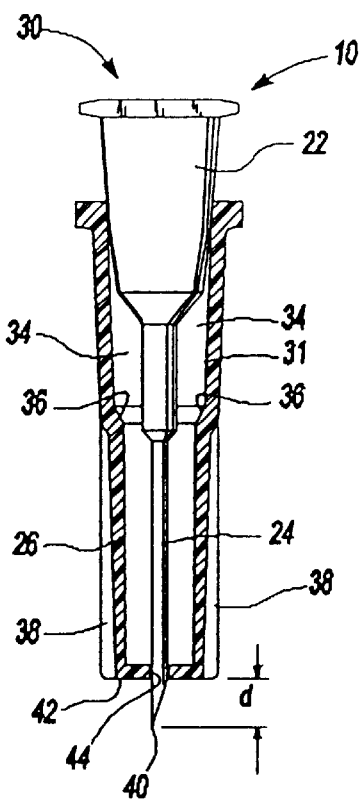
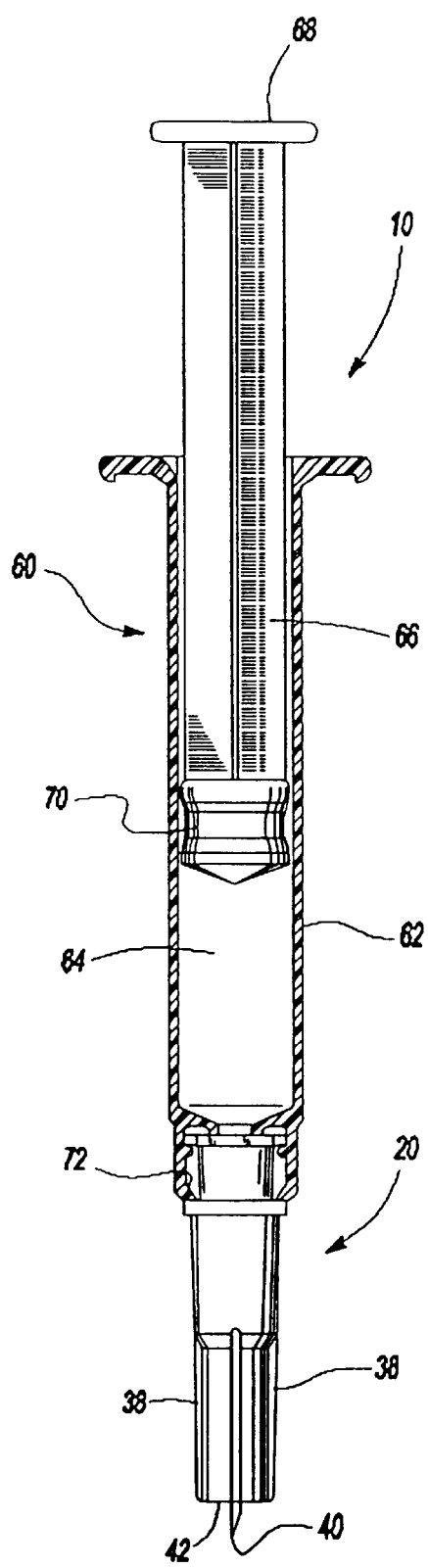

METHOD OF INTRADERMALLY INJECTING SUBSTANCES

REFERENCE TO RELATED APPLICATIONS

The present application is a continuation U.S. patent application Ser. No. 10/044,504 filed on Jan. 10, 2002, which is a continuation-in-part of U.S. patent application Ser. No. 09/835,243, filed on Apr. 13, 2001, now U.S. Pat. No. 6,569,143, which is a continuation-in-part of U.S. patent application Ser. No. 09/417,671, filed on Oct. 14, 1999, now U.S. Pat. No. 6,494,865.

FIELD OF THE INVENTION

The present invention generally relates to a method for delivering substances such as drugs, vaccines and the like used in the prevention, diagnosis, alleviation, treatment, or cure of diseases into the skin of an animal using an injection device having a needle cannula and a limiter for engaging the surface of the skin and limiting penetration of the tip of the needle cannula into the skin, and more specifically to a method for injecting such substances intradermally, i.e., preferably from approximately 1.0 mm to approximately 2.0 mm, and most preferably around 1.5 mm±0.2 mm to 0.3 mm, such that the substance is injected into the dermis layer of the animal. In addition, the method of the present invention includes fixing the orientation of the needle cannula, i.e., so that the needle cannula is preferably generally perpendicular to the plane of the skin engaging surface of the limiter within about fifteen degrees, and the skin engaging surface is generally flat.

BACKGROUND OF THE INVENTION

Intradermal injections are used for delivering a variety of substances. Many of these substances have proven to be more effectively absorbed into or react with the immune response system of the body when injected intradermally. Recently, clinical trials have shown that hepatitis B vaccines administered intradermally are more imunogenic than if administered intramuscularly. In addition, substances have been injected intradermally for diagnostic testing, such as, for example using what is known in the art as the "Mantoux test" to determine the immunity status of the animal against tuberculosis and the immediate hypersensitivity status of Type I allergic diseases.

An intradermal injection is made by delivering the substance into the epidermis and upper layers of the dermis. Below the dermis layer is subcutaneous tissue (also sometimes referred to as the hypodermis layer) and muscle tissue, in that order. There is considerable variation in the skin thickness both between individuals and within the same individual at different sites of the body. Generally, the outer skin layer, epidermis, has a thickness between 50–200 microns, and the dermis, the inner and thicker layer of the skin, has a thickness between 1.5–3.5 mm. Therefore, a needle cannula that penetrates the skin deeper than about 3.0 mm has a potential of passing through the dermis layer of the skin and making the injection into the subcutaneous region, which may result in an insufficient immune response, especially where the substance to be delivered intradermally has not been indicated for subcutaneous injection. Also, the needle cannula may penetrate the skin at too shallow a depth to deliver the substance and result in what is commonly known in the art as a "wet injection" because of reflux of the substance from the injection site.

The standard procedure for making an intradermal injection is known to be difficult to perform, and therefore dependent upon experience and technique of the healthcare worker. This procedure is recommended to be performed by stretching the skin, orienting the bevel of a 26 Gauge short bevel needle cannula upwardly and inserting the needle cannula to deliver a volume of 0.5 ml or less of the substance into the skin of an animal with the needle cannula being inserted into the skin at an angle varying from around 10–15 degrees relative to the plane of the skin to form a blister or wheal in which the substance is deposited or otherwise contained. Accordingly, the technique utilized to perform the standard intradermal injection is difficult and requires the attention of a trained nurse or medical doctor. This procedure also makes it essentially impossible to self-administer an intradermal injection. Inserting the needle to a depth greater than about 3.0 mm typically results in a failed intradermal injection because the substance being expelled through the cannula will be injected into the subcutaneous tissue of the animal. Further, the present method is not suitable for self-administration of intradermal injections.

The most frequent cause of a failed intradermal injection is derived from inserting the needle into the skin at an angle greater than 15 degrees. A further cause of error is derived from pinching rather than stretching the skin in the area of the injection, which is normally done when giving a subcutaneous rather than an intradermal injection. Pinching increases the likelihood of giving a subcutaneous injection. Procedural errors as described above result in delivering the contents of the injection into the subcutaneous layer, which can reduce the effectiveness of the injection, as well as possibly deliver the substance in a way not approved for delivery. Intradermal injections performed by using the standard procedure also are known to cause a significant amount of pain to the recipient of the injection because the needle cannula is inserted into the skin at an angle of about 10–15 degrees. By inserting the needle cannula at this angle, about 5 mm to about 6 mm of the needle is actually inserted into the skin. This results in a significant disruption of the pain receptors dispersed throughout the upper layers of the skin.

Accordingly, there has been a long felt need for a simplified method of performing an intradermal injection of substances which overcomes the problems and limitations associated with conventional methods, especially including reducing the probability of error and pain caused from the injection by making such injections less dependent upon experience and technique. In addition, there has been a need to limit the depth of penetration of the needle cannula into the skin of the animal to avoid entry into the subcutaneous layer of the skin as well as reliably fixing the orientation of the needle cannula relative to the skin. Also, there has been a need to apply pressure to the skin of the animal to facilitate formation of the blister or wheal in the skin in which the substance is deposited or otherwise contained and avoid wet injections.

SUMMARY OF THE INVENTION AND ADVANTAGES

In contrast to the conventional methods discussed above, it has been found by the applicant that a method of intradermally injecting substances into the skin to obtain systemic delivery or an immune response can be used in accordance with the present invention to effectively and reliably deliver such substances intradermally. Specifically, the method includes fixing the orientation of the needle cannula relative to the skin and engaging the surface of the skin to limit the depth of penetration of the needle cannula into the skin, i.e., preferably from approximately 1.0 mm to approximately 2.0 mm, and most preferably around 1.5 mm±0.2 mm to 0.3 mm, to avoid entry into the subcutaneous layer. In addition, the method includes applying pressure to the surface of the skin to facilitate delivery of the substance, particularly formation of a blister or wheal in the skin in which the substance is deposited or otherwise contained. Further, the pressure applied masks the pain derived from the intradermal injection by stimulating the muscle fibers to block the pain receptors. Many substances have proven to be more effective when injected intradermally in the prevention, diagnosis, alleviation, treatment, or cure of diseases. These include several drugs and vaccines such as, for example, influenza vaccines, hepatitis B vaccine, rabies vaccines tuberculin test substance and many others. These vaccines, drugs and the like will hereinafter be referred to as substances. It is also possible to self-administer intradermal injections by the method of this invention.

The hypodermic needle assembly set forth above includes the elements necessary to perform the present invention directed to an improved method of making an intradermal injection into the skin of an animal including the steps of providing a drug delivery device including a needle cannula having a forward needle tip and the needle cannula being in fluid communication with a substance contained in the drug delivery device and including a limiter portion surrounding the needle cannula and the limiter portion including a skin engaging surface, with the needle tip of the needle cannula extending from the limiter portion beyond the skin engaging surface a distance equal to approximately 0.5 mm to approximately 3.0 mm and the needle cannula having a fixed angle of orientation relative to a plane of the skin engaging surface of the limiter portion, inserting the needle tip into the skin of an animal and engaging the surface of the skin with the skin engaging surface of the limiter portion, such that the skin engaging surface of the limiter portion limits penetration of the needle cannula tip into the dermis layer of the skin of the animal, and expelling the substance from the drug delivery device through the needle cannula tip into the skin of the animal to expose the injected substance to the microcirculatory blood vasculature and the lymphatic plexuses.

In the preferred method, the substance is selected from the group consisting of drugs, vaccines and the like used in the prevention, diagnosis, alleviation, treatment, or cure of diseases. In addition, the fixed angle of orientation of the needle cannula is further defined as being generally perpendicular to the plane of the skin engaging surface of the limiter portion within about fifteen degrees, and most preferably within about five degrees, substantially ninety degrees relative to the plane of the skin engaging surface of the limiter portion. In addition, the drug delivery device includes a syringe having a barrel and a plunger rod preferably including a stopper received within the barrel therein and the plunger rod being depressable to expel the substance from the delivery device through the tip of the needle cannula, with the barrel including a barrel tip and the needle cannula forms part of a needle assembly attachable to and in fluid communication with the barrel tip.

Also, the preferred embodiment of the method includes the step of selecting an injection sight on the skin of the animal and includes the step of cleaning the injection sight on the skin of the animal prior to expelling the substance from the drug delivery device into the skin of the animal. In addition, the method includes the step of filling the drug delivery device with the substance. Further, the method includes the steps of pressing the skin engaging surface of the limiter portion against the skin of the animal and applying pressure, thereby stretching the skin of the animal, and withdrawing the needle cannula from the skin after injecting the substance. Still further, the step of inserting the forward tip into the skin is further defined by inserting the forward tip into the skin to a depth of from approximately 1.0 mm to approximately 2.0 mm, and most preferably into the skin to a depth of 1.5 mm±0.2 to 0.3 mm. The preferred substance comprises an influenza vaccine, a hepatitis B vaccine, a rabies vaccine, a cancer vaccine, a genetic based vaccine or a tuberculin test substance.

The preferred substance includes a combination of the drugs or vaccines. In addition, the preferred method includes the addition of a substance selected from a combination of vaccines against: (i) measles, mumps and rubella, (ii) diphtheria, tetanus and acellular pertussis, (iii) hepatitis A and hepatitis B, (iv) haemophilus influenza B, diphtheria, tetanus and acellular pertussis, (v) haemophilus influenza B, hepatitis B, diphtheria, tetanus and a cellular pertussis, and (vi) haemophilus influenza B, inactivated polio, diphtheria, tetanus and acellular pertussis, which are commonly delivered in combination to the subcutaneous and/or intramuscular space.

In addition, the present invention is directed to a method of making an intradermal injection with a drug delivery device having a limiter with a skin engaging surface limiting the depth a needle cannula can be inserted into the skin of an animal to obtain systemic delivery or an immune response or including the steps of exposing a forward tip of the needle cannula extending from a limiter beyond a skin engaging surface a distance equal to approximately 0.5 mm to approximately 3.0 mm and the needle cannula having a fixed angle of orientation relative to the skin engaging surface of the limiter, inserting the forward tip of the needle cannula into the skin of the animal at until the skin engaging surface contacts the skin of the animal, and expelling a substance from the device into the dermis layer of the skin of the animal to expose the injected substance to the microcirculatory blood vasculature and the lymphatic plexuses.

In the preferred embodiment of the method, the step of inserting the forward tip into the skin of the animal is further defined by inserting the forward tip into the skin at an angle being generally perpendicular to the skin within about fifteen degrees, with the angle most preferably being generally ninety degrees to the skin, within about five degrees, and the fixed angle of orientation relative to the skin engaging surface is further defined as being generally perpendicular. In the preferred embodiment, the limiter surrounds the needle cannula, having a generally planar flat skin engaging surface. Also, the drug delivery device comprises a syringe having a barrel and a plunger received within the barrel and the plunger being depressable to expel the substance from the delivery device through the forward tip of the needle cannula.

In the preferred embodiment of the method of the present invention, expelling the substance from the delivery device is further defined by grasping the hypodermic needle with a first hand and depressing the plunger with an index finger of a second hand and expelling the substance from the delivery device by grasping the hypodermic needle with a first hand and depressing the plunger on the hypodermic needle with a thumb of a second hand, with the step of inserting the forward tip into the skin of the animal further defined by pressing the skin of the animal with the limiter. In addition, the method may includes the step of attaching a needle assembly to a tip of the barrel of the syringe with the needle assembly including the needle cannula and the limiter, and includes the step of exposing the tip of the barrel before attaching the needle assembly thereto by removing a cap from the tip of the barrel. Alternatively, the step of inserting the forward tip of the needle into the skin of the animal may be further defined by simultaneously grasping the hypodermic needle with a first hand and pressing the limiter against the skin of the animal thereby stretching the skin of the animal, and expelling the substance by depressing the plunger with an index finger of the first hand or expelling the substance by depressing the plunger with a thumb of the first hand. The method further includes withdrawing the forward tip of the needle cannula from the skin of the animal after the substance has been injected into the skin of the animal. Still further, the method includes inserting the forward tip into the skin preferably to a depth of from approximately 1.0 mm to approximately 2.0 mm, and most preferably to a depth of 1.5 mm±0.2 to 0.3 mm. Also, the step of expelling the substance from the device into the dermis layer of the skin includes expelling a small volume of air from the device into the dermis layer before expelling the substance.

Also, the substance intradermally delivered in accordance with the method of the present invention is selected from the group consisting of drugs, vaccines and the like used in the prevention, diagnosis, alleviation, treatment, or cure of disease, with the drugs including Alpha-1 anti-trypsin, Anti-Angiogenesis agents, Antisense, butorphanol, Calcitonin and analogs, Ceredase, COX-II inhibitors, dermatological agents, dihydroergotamine, Dopamine agonists and antagonists, Enkephalins and other opioid peptides, Epidermal growth factors, Erythropoietin and analogs, Follicle stimulating hormone, G-CSF, Glucagon, GM-CSF, granisetron, Growth hormone and analogs (including growth hormone releasing hormone), Growth hormone antagonists, Hirudin and Hirudin analogs such as hirulog, IgE suppressors, Insulin, insulinotropin and analogs, Insulin-like growth factors, Interferons, Interleukins, Leutenizing hormone, Leutenizing hormone releasing hormone and analogs, Low molecular weight heparin, M-CSF, metoclopramide, Midazolam, Monoclonal antibodies, Narcotic analgesics, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, Thrombolytics, Tissue plasminogen activators, TNF-, and TNF-antagonist, the vaccines, with or without carriers/adjuvants, including prophylactics and therapeutic antigens (including but not limited to subunit protein, peptide and polysaccharide, polysaccharide conjugates, toxoids, genetic based vaccines, live attenuated, reassortant, inactivated, whole cells, viral and bacterial vectors) in connection with, addiction, arthritis, cholera, cocaine addiction, diphtheria, tetanus, HIB, Lyme disease, meningococcus, measles, mumps, rubella, varicella, yellow fever, Respiratory syncytial virus, tick borne japanese encephalitis, pneumococcus, streptococcus, typhoid, influenza, hepatitis, including hepatitis A, B, C and E, otitis media, rabies, polio, HIV, parainfluenza, rotavirus, Epstein Barr Virus, CMV, chlamydia, non-typeable haemophilus, moraxella catarrhalis, human papilloma virus, tuberculosis including BCG, gonorrhoea, asthma, atheroschlerosis malaria, *E-coli*, Alzheimers, *H. Pylori*, salmonella, diabetes, cancer, herpes simplex, human papilloma and the like other substances including all of the major therapeutics such as agents for the common cold, Anti-addiction, anti-allergy, anti-emetics, anti-obesity, antiosteoporeteic, anti-infectives, analgesics, anesthetics, anorexics, antiarthritics, antiasthmatic agents, anticonvulsants, anti-depressants, antidiabetic agents, antihistamines, anti-inflammatory agents, antimigraine preparations, antimotion sickness preparations, antinauseants, antineoplastics, antiparkinsonism drugs, antipruritics, antipsychotics, antipyretics, anticholinergics, benzodiazepine antagonists, vasodilators, including general, coronary, peripheral and cerebral, bone stimulating agents, central nervous system stimulants, hormones, hypnotics, immunosuppressives, muscle relaxants, parasympatholytics, parasympathomimetrics, prostaglandins, proteins, peptides, polypeptides and other macromolecules, psychostimulants, sedatives, sexual hypofunction and tranquilizers and major diagnostics such as tuberculin and other hypersensitivity agents.

Another embodiment of the method of the present invention of making an intradermal injection into the skin of an animal includes the steps of providing a drug delivery device with a prefillable container including a needle cannula having a forward needle tip and the needle cannula being in fluid communication with a substance contained in the prefillable container and including a limiter portion surrounding the needle cannula and the limiter portion including a skin engaging surface, with the needle tip of the needle cannula extending from the limiter portion beyond the skin engaging surface and the needle cannula having a fixed angle of orientation relative to a plane of the skin engaging surface of the limiter portion, inserting the needle tip into the skin of an animal and engaging the surface of the skin with the skin engaging surface of the limiter portion such that the skin engaging surface of the limiter portion limits penetration of the needle tip into the dermis layer of the skin of the animal, and expelling a small volume of air and the substance from the drug delivery device through the needle tip into the skin of the animal to expose the injected substance to the microcirculatory blood vascularity and the lymphatic plexuses where the substance can be taken up, absorbed or can interact with the cells to obtain systemic delivery or an immune response in cases where the substance is either a drug or one or more vaccines.

BRIEF DESCRIPTION OF THE DRAWINGS

Other advantages of the present invention will be readily appreciated and apparent to those skilled in the art as the same becomes better understood by reference to the following detailed description when considered in connection with the accompanying drawings wherein:

FIG. 1 is an exploded, perspective illustration of a needle assembly designed according to this invention.

FIG. 2 is a partial cross-sectional illustration of the embodiment of FIG. 1.

FIG. 3 shows the embodiment of FIG. 2 attached to a syringe body to form an injection device.

DETAILED DESCRIPTION OF THE PREFERRED EMBODIMENTS

Figure 4:
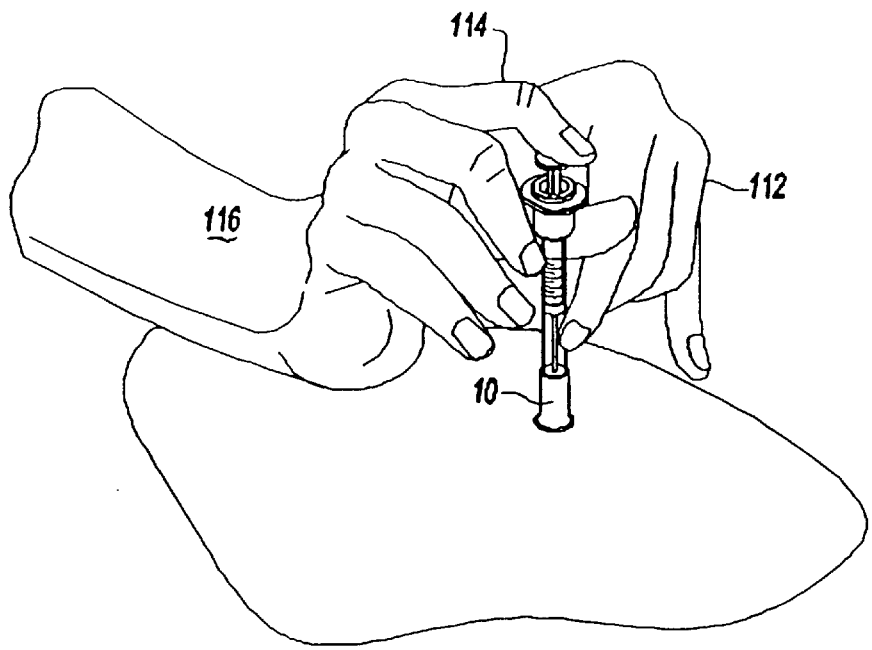
FIG. 4 is a perspective view of one technique for making the intradermal injection of the present invention.
Figure 5:
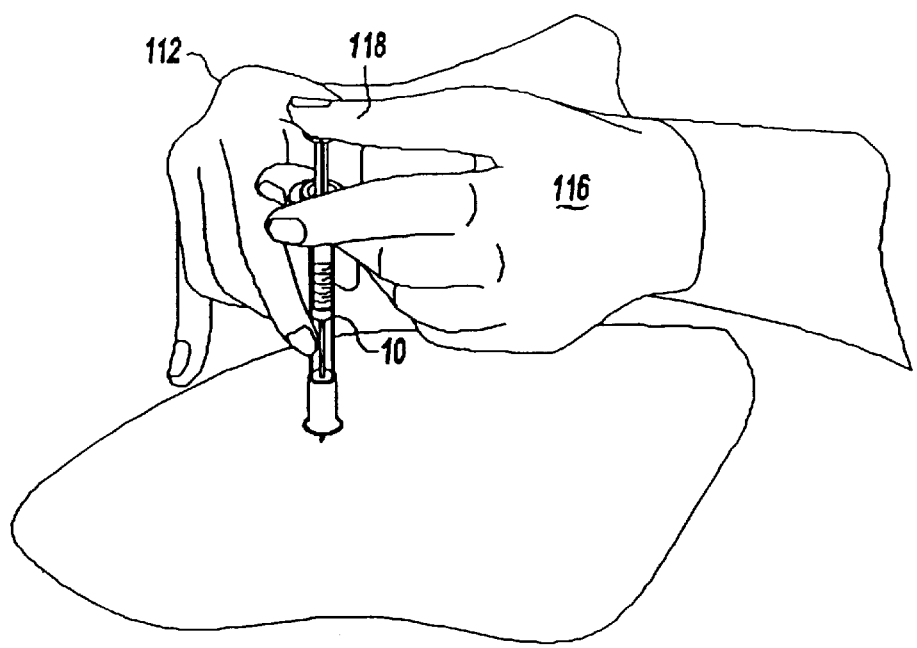
FIG. 5 is a perspective view of a second technique for making the intradermal injection of the present invention.
Figure 6:
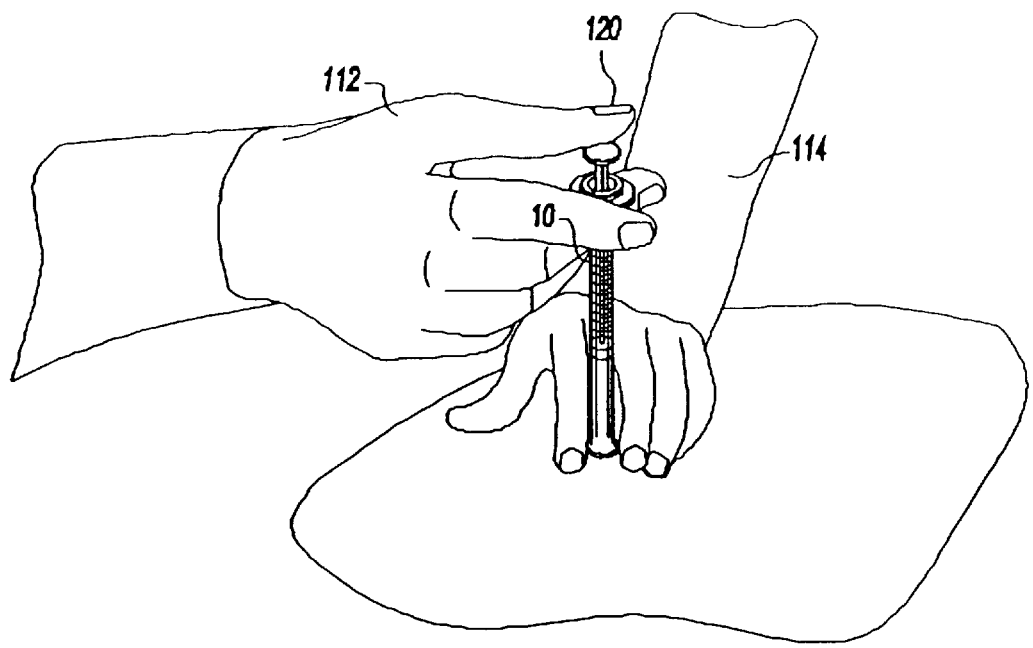
FIG. 6 is a perspective view of a third technique for making the intradermal injection of the present invention.
Figure 7:
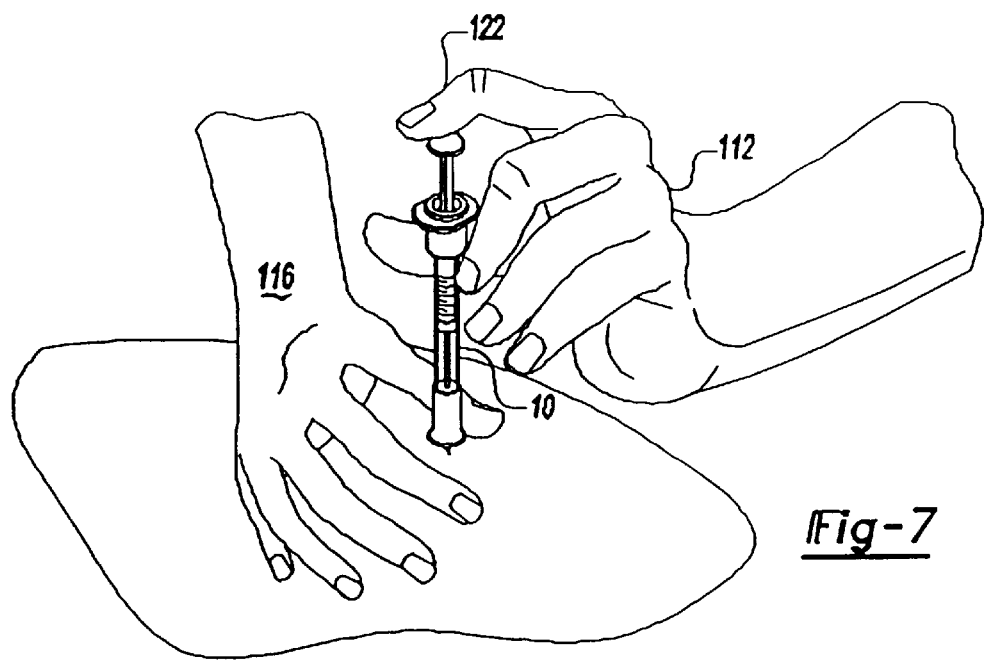
FIG. 7 is a perspective view of a fourth technique for making the intradermal injection of the present invention.

FIGS. 1–3 of the drawings illustrate an example of a drug delivery device which can be used to practice the methods of the present invention for making intradermal injections illustrated in FIGS. 4–7. The device 10 illustrated in FIGS. 1–3 includes a needle assembly 20 which can be attached to a syringe barrel 60. Other forms of delivery devices may be used including pens of the types disclosed in U.S. Pat. No. 5,279,586, U.S. patent application Ser. No. 09/027,607 and PCT Application No. WO 00/09135, the disclosure of which are hereby incorporated by reference in their entirety. The method of the present invention can be used to intradermally inject substances, other than food, such as drugs, vaccines and the like used in the prevention, diagnosis, alleviation, treatment, or cure of disease into the skin of an animal such as a human, referred to collectively herein as "substances".

The needle assembly 20 includes a hub 22 that supports a needle cannula 24. The limiter 26 receives at least a portion of the hub 22 so that the limiter 26 generally surrounds the needle cannula 24 as best seen in FIG. 2.

One end 30 of the hub 22 is able to be secured to a receiver 32 of a syringe. A variety of syringe types for containing the substance to be intradermally delivered according to the present invention can be used with a needle assembly designed, with several examples being given below. The opposite end of the hub 22 preferably includes extensions 34 that are nestingly received against abutment surfaces 36 within the limiter 26. A plurality of ribs 38 preferably are provided on the limiter 26 to provide structural integrity and to facilitate handling the needle assembly 20.

By appropriately designing the size of the components, a distance "d" between a forward end or tip 40 of the needle 24 and a skin engaging surface 42 on the limiter 26 can be tightly controlled. The distance "d" preferably is in a range from approximately 0.5 mm to approximately 3.0 mm, and most preferably around 1.5 mm±0.2 mm to 0.3 mm. When the forward end 40 of the needle cannula 24 extends beyond the skin engaging surface 42 a distance within that range, an intradermal injection is ensured because the needle is unable to penetrate any further than the typical dermis layer of an animal. Typically, the outer skin layer, epidermis, has a thickness between 50–200 microns, and the dermis, the inner and thicker layer of the skin, has a thickness between 1.5–3.5 mm. Below the dermis layer is subcutaneous tissue (also sometimes referred to as the hypodermis layer) and muscle tissue, in that order.

As can be best seen in FIG. 2, the limiter 26 includes an opening 44 through which the forward end 40 of the needle cannula 24 protrudes. The dimensional relationship between the opening 44 and the forward end 40 can be controlled depending on the requirements of a particular situation. In the illustrated embodiment, the skin engaging surface 42 is generally planar or flat and continuous to provide a stable placement of the needle assembly 20 against an animal's skin. Although not specifically illustrated, it may be advantageous to have the generally planar skin engaging surface 42 include either raised portions in the form of ribs or recessed portions in the form of grooves in order to enhance stability or facilitate attachment of a needle shield to the needle tip 40. Additionally, the ribs 38 along the sides of the limiter 26 may be extended beyond the plane of the skin engaging surface 42.

Regardless of the shape or contour of the skin engaging surface 42, the preferred embodiment includes enough generally planar or flat surface area that contacts the skin to facilitate stabilizing the injector relative to the animal's skin. In the most preferred arrangement, the skin engaging surface 42 facilitates maintaining the injector in a generally perpendicular orientation relative to the skin surface and facilitates the application of pressure against the skin during injection. Thus, in the preferred embodiment, the limiter has dimension or outside diameter of at least 5 mm. The major dimension will depend upon the application and packaging limitations, but a convenient diameter is less than 15 mm or more preferably 11–12 mm.

It is important to note that although FIGS. 1 and 2 illustrate a two-piece assembly where the hub 22 is made separate from the limiter 26, a device for use in connection with the invention is not limited to such an arrangement. Forming the hub 22 and limiter 26 integrally from a single piece of plastic material is an alternative to the example shown in FIGS. 1 and 2. Additionally, it is possible to adhesively or otherwise secure the hub 22 to the limiter 26 in the position illustrated in FIG. 2 so that the needle assembly 20 becomes a single piece unit upon assembly.

Having a hub 22 and limiter 26 provides the advantage of making an intradermal needle practical to manufacture. The preferred needle size is a small Gauge hypodermic needle, commonly known as a 30 Gauge or 31 Gauge needle. Having such a small diameter needle presents a challenge to make a needle short enough to prevent undue penetration beyond the dermis layer of an animal. The limiter 26 and the hub 22 facilitate utilizing a needle 24 that has an overall length that is much greater than the effective length of the needle, which penetrates the individual's tissue during an injection. With a needle assembly designed in accordance herewith, manufacturing is enhanced because larger length needles can be handled during the manufacturing and assembly processes while still obtaining the advantages of having a short needle for purposes of completing an intradermal injection.

FIG. 3 illustrates the needle assembly 20 secured to a drug container such as a syringe 60 to form the device 10. A generally cylindrical syringe body 62 can be made of plastic or glass as is known in the art. The syringe body 62 provides a reservoir 64 for containing the substance to be administered during an injection. A plunger rod 66 has a manual activation flange 68 at one end with a stopper 70 at an opposite end as known in the art. Manual movement of the plunger rod 66 through the reservoir 64 forces the substance within the reservoir 64 to be expelled out of the end 40 of the needle as desired.

The hub 22 can be secured to the syringe body 62 in a variety of known manners. In one example, an interference fit is provided between the interior of the hub 22 and the exterior of the outlet port portion 72 of the syringe body 62. In another example, a conventional Luer fit arrangement is provided to secure the hub 22 on the end of the syringe 60. As can be appreciated from FIG. 3, such needle assembly designed is readily adaptable to a wide variety of conventional syringe styles.

This invention provides an intradermal needle injector that is adaptable to be used with a variety of syringe types. Therefore, this invention provides the significant advantage of facilitating manufacture and assembly of intradermal needles on a mass production scale in an economical fashion.

Having described the intradermal delivery device including the needle assembly 20 and drug container 60, its operation and use in practicing the methods of the present invention for intradermally injecting substances is described below.

Prior to inserting the needle cannula 24, an injection site upon the skin of the animal is selected and cleaned. Subsequent to selecting and cleaning the site, the forward end 40 of the needle cannula 24 is inserted into the skin of the animal at an angle of generally 90 degrees until the skin engaging surface 42 contacts the skin. The skin engaging surface 42 prevents the needle cannula 42 from passing through the dermis layer of the skin and injecting the substance into the subcutaneous layer.

While the needle cannula 42 is inserted into the skin, the substance is intradermally injected. The substance may be prefilled into the syringe 60, either substantially before and stored therein just prior to making the injection. Several variations of the method of performing the injection may be utilized depending upon individual preferences and syringe type. In any event, the penetration of the needle cannula 42 is most preferably no more than about 1.5 mm because the skin engaging surface 42 prevents any further penetration.

Also, during the administration of an intradermal injection, the forward end 40 of the needle cannula 42 is embedded in the dermis layer of the skin which results in a reasonable amount of back pressure during the injection of the substance. This back pressure could be on the order of 76 psi. In order to reach this pressure with a minimal amount of force having to be applied by the user to the plunger rod 66 of the syringe, a syringe barrel 60 with a small inside diameter is preferred such as 0.183" (4.65 mm) or less. The method of this invention thus includes selecting a syringe for injection having an inside diameter of sufficient width to generate a force sufficient to overcome the back pressure of the dermis layer when the substance is expelled from the syringe to make the injection.

In addition, since intradermal injections are typically carried out with small volumes of the substance to be injected, i.e., on the order of no more than 0.5 ml, and preferably around 0.1 ml, a syringe barrel 60 with a small inside diameter is preferred to minimize dead space which could result in wasted substance captured between the stopper 70 and the shoulder of the syringe after the injection is completed. Also, because of the small volumes of substance, on the order of 0.1 ml, a syringe barrel with a small inside diameter is preferred to minimize air head space between the level of the substance and the stopper 70 during process of inserting the stopper. Further, the small inside diameter enhances the ability to inspect and visualize the volume of the substance within the barrel of the syringe.

Figure 8:
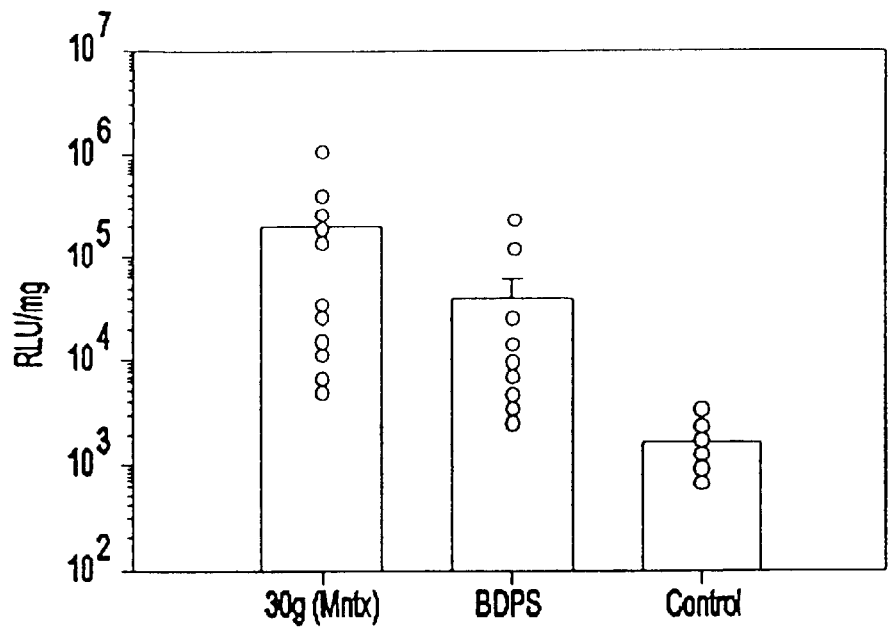
FIG. 8 is a bar chart showing the B-gal expression levels of the clinical trials on swine skin.
Figure 9:
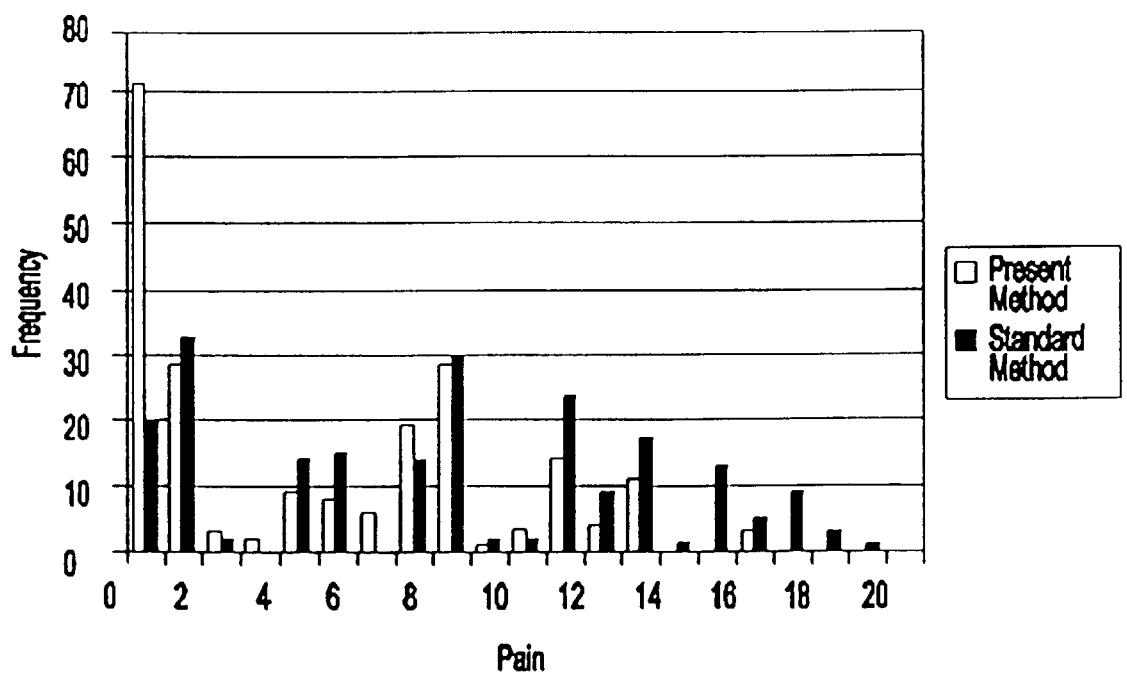
FIG. 9 is a histogram showing the results of a survey of the subjects pain perception relevant from the human clinical trial.

Several variations of performing the intradermal injection of the present invention (present method) were proven effective during clinical trials, the results of which will be explained below. As shown in FIG. 8, the syringe 60 may be grasped with a first hand 112 and the plunger 66 depressed with the forefinger 114 of a second hand 116. Alternatively, as shown in FIG. 9 the plunger 66 may be depressed by the thumb 118 of the second hand 116 while the syringe 60 is held by the first hand. In each of these variations, the skin of the animal is depressed, and stretched by the skin engaging surface 42 on the limiter 26. The skin is contacted by neither the first hand 112 nor the second hand 116.

Figure 10:
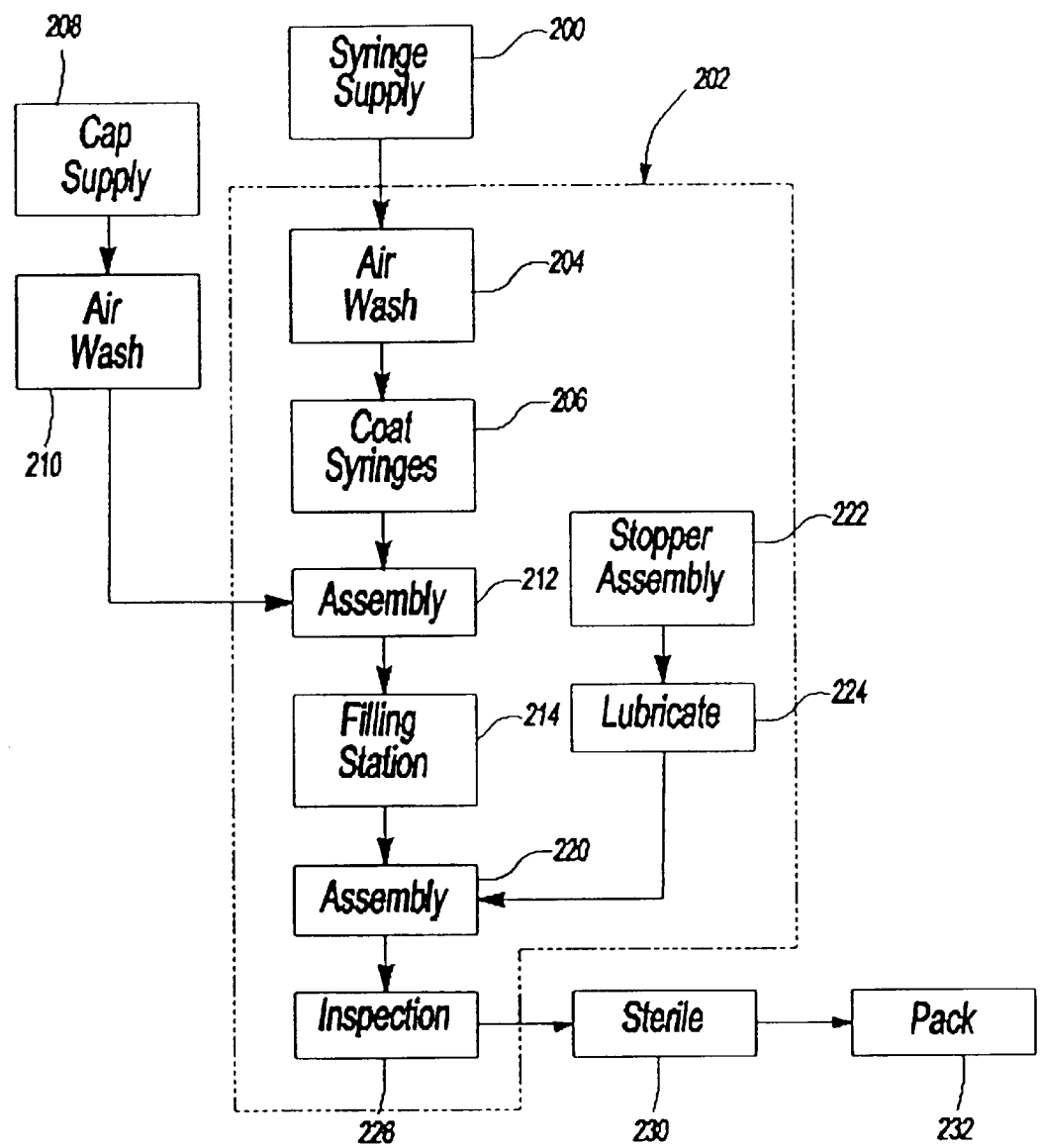
FIG. 10 is a flow chart diagram that schematically illustrates preparation of the device for use in intradermally injecting substances, including filling the device with the substance.

An additional variation has proven effective for administering the intradermal injection of the present invention. This variation includes gripping the syringe 60 with the same hand that is used to depress the plunger 66. FIG. 10 shows the syringe 60 being gripped with the first hand 112 while the plunger is simultaneously depressed with the thumb 120 of the first hand 112. This variation includes stretching the skin with the second hand 114 while the injection is being made. Alternatively, as shown in FIG. 11, the grip is reversed and the plunger is depressed by the forefinger 122 of the first hand 112 while the skin is being stretched by the second hand 116. However, it is believed that this manual stretching of the skin is unnecessary and merely represents a variation out of habit from using the standard technique.

In each of the variations described above, the needle cannula 24 is inserted only about 1.5 mm into the skin of the animal. Subsequent to administering the injection, the needle cannula 24 is withdrawn from the skin and the syringe 60 and needle assembly 20 are disposed of in an appropriate manner. Each of the variations were utilized in clinical trials to determine the effectiveness of both the needle assembly 20 and the present method of administering the intradermal injection.

The feasibility of the present method was also proven effective in animal tests on live swine skin. 50 $\mu$g of naked plasmid DNA encoding the reporter gene, b-galactosidase (b-gal), in fifty $\mu$l volume was delivered intradermally via "rapid bolus" (approximately 2 $\mu$l/sec.). Full thickness skin biopsies were removed at twenty four hours and evaluated for b-gal activity. Twelve separate sites were administered the intradermal injections on three separate Yorkshire swine, i.e., four sites were evaluated for each group on each swine. Negative controls consisted of delivery of an equivalent dose of an unrelated plasmid DNA. Background b-gal activity in the control group combines data from 30 Gauge needle cannula delivered with the standard procedure and 26.6 Gauge needle utilizing the limiter 26 and the present method. There was no discernable difference detected, as there was no difference in activity between the control groups.

Mean b-gal activity was determined for both the standard procedure and the technique of the present method. Mean b-gal activity is represented by the bars, and activity within individual skin sites is represented by the dots on the chart shown in FIG. 8. Although there was high variability in each of the groups, standard procedure, present method, and control, there was a significant increase in b-gal activity in the standard procedure and the present technique compared to the control group. There was no statistical difference in b-gal activity between the standard procedure and the present method. Therefore, it was proven during the animal tests conducted on swine skin that the present method could be used to deliver an intradermal injection at least as effectively as the standard procedure.

Subsequent to the swine studies, a clinical trial was conducted on human volunteers to evaluate the effectiveness of the procedure of the present invention. Twelve nurses administered intradermal injections to 108 healthy subjects. Six of the nurses were very experienced in giving intradermal injections, and six of the nurses only occasionally gave intradermal injections in which case they only had a baseline competency in giving injections prior to the study. Each of the nurses received training in the form of videos and practice upon a rubber arm on both techniques for making the intradermal injection prior to initiating the trial.

The subjects comprised various ethnic groups to determine if ethnicity would have any impact upon functionality. These groups included:

| Ethnicity | Number (percent) |
|---|---|
| Caucasian | 67 (16.7%) |
| African American | 22 (20.4%) |
| Latino | 12 (11.1%) |
| Asian/Pacific | 7 (6.5%) |

Eighteen (16.7%) of the subjects were older than sixty years of age.

A 26 Gauge ⅜ inch needle cannula with an intradermal bevel was utilized for the standard procedure, which includes inserting the needle into the skin at a fifteen degree angle in order to avoid delivering a subcutaneous injection. A 30 Gauge ½ needle with an intradermal bevel was used with the limiter 26 to administer the intradermal injection utilizing the present method (generally ninety degree insertion of the needle cannula) for comparison with the standard procedure. Each of the nurses were instructed to insert the needle cannula into the skin until the skin engaging surface 42 made tight contact with the skin, compressing the skin. Each nurse used one of the variations associated with the limiter 42 and described above to administer the intradermal injection using the present method. The variation chosen by each nurse was based upon individual preference.

Each syringe was filled with 110 μl of saline solution. The saline solution was delivered via separate injections into the volar forearm and deltoid region. To determine the effectiveness of the injection, the site into which the injection was made was examined for a satisfactory tense white wheal resulting from the injection of the saline solution. The existence of a white wheal indicates a successful injection has been made.

Other variables were analyzed during the trial including the amount of pain experienced by each of the subjects following the saline injection, the subjects preference for the variation used, and the nurses preferences.

A tuberculin syringe was filled with 110 μl of saline solution. The air was purged and the filling needle was removed prior to attaching the appropriate intradermal needle as defined by a randomization schedule developed for the trial. Each subject was administered eight intradermal injections, two with 100 μl of saline solution into the right and left volar forearms, and two with 100 μl of saline into the right and left deltoid region. One injection from each pair was given utilizing the present method of the instant invention and one injection was given utilizing the standard procedure. Each of the injections were administered according to a Randomized Schedule developed for the clinical trial. Good Clinical Practice and Universal Precautions was adhered to during each of the procedures.

An injection was considered acceptable if a tense white wheal was observed soon after the injection was completed. Completeness of the injection and post-injection bleeding were also evaluated immediately following each injection. The pain perceived by the subject was also evaluated immediately after each injection. The subjects were also asked which intradermal method was preferred at the conclusion of the each session.

The most significant improvement over the standard procedure was the decrease in the amount of pain perceived by each subject. Pain was measured on a twenty point, Gracely Box SL Scale. Each subject was asked to select a point on the table listed below that corresponds to the amount of pain perceived:

TABLE 1

| Score | Sensation |
|---|---|
| 0 | No Pain Sensation |
| 1 | Faint (pain sensation) |
| 2 | |
| 3 | |
| 4 | Very Weak |
| 5 | Weak |
| 6 | |
| 7 | Very Mild |
| 8 | Mild |
| 9 | |
| 10 | |
| 11 | Moderate |
| 12 | Barely Strong |
| 13 | Slightly Intense |
| 14 | |
| 15 | Strong |
| 16 | Intense |
| 17 | Very Intense |
| 18 | Extremely Intense |
| 19 | |
| 20 | |

FIG. 9 shows a histogram of the pain perceived by each of the subjects corresponding to the method used to make the intradermal injection. The present method proved to be significantly less painful for the subjects than the standard method. This is believed to be in part due to the reduction in the length of needle cannula that is inserted into the skin. The present method results in only 1.5 mm of needle cannula being inserted into the skin. The standard procedure, because of the injection angle of fifteen degrees, results in the needle cannula being inserted at least twice that amount to reach the depth required to make the injection. Statistically, the present method proved much less painful than the standard procedure. The table below indicates that the mean pain score for the standard procedure is forty percent higher than present method described above. The median pain score for the standard procedure proved to be twice that of the present method.

| Delivery Method | Mean | Median | Standard Dev. |
|---|---|---|---|
| Standard Procedure | 7.720 | 8.000 | 5.423 |
| Present Method | 4.460 | 4.000 | 4.580 |

A visual inspection of the wheal formation subsequent to each intradermal injection indicated that there was no discernable difference in results between the two methods of making the intradermal injection. A binary analysis was made for each injection site. If no wheal formed after the intradermal injection was made, a numerical value of zero was assigned. If a tight white wheal formed after the intradermal injection was made, a numerical value of one was assigned. Table 2 listed below indicates the results of the visual inspection:

TABLE 2

| Delivery Method | Zero | One | Number of sites |
|---|---|---|---|
| Standard Procedure | 42 | 172 | 214 |
| Present Method | 46 | 170 | 216 |

The data collected indicates that with respect to forming a tight white wheal the present method performed generally as well as the standard procedure.

Each of the nurses was surveyed with respect to their preference for the standard procedure or the present method with respect to a particular injection. The nurses indicated a substantial preference for the present method in response to several inquiries. The first was an inquiry as to which intradermal injection was thought to be best relative to each patient. Table 3 indicates the nurses had a significant overall preference for the present method:

TABLE 3

| Delivery Method | Number |
| --- | --- |
| Standard Procedure | 24 |
| Present Method | 81 |
| No Preference | 3 |
| Total Responses | 108 |

In response to an inquiry as to the easiest method to administer an intradermal injection, the nurses indicated a significant preference for the present method:

TABLE 4

| Delivery Method | Number |
| --- | --- |
| Standard Procedure | 5 |
| Present Method | 99 |
| No Preference | 4 |
| Total Responses | 108 |

In response to an inquiry as to the overall preference between the standard procedure or the present method the nurses indicated a significant preference for the present method:

TABLE 5

| Delivery Method | Number |
| --- | --- |
| Standard Procedure | 3 |
| Present Method | 87 |
| No Preference | 18 |
| Total | 108 |

When a preference was requested between the standard procedure and the present method relative to a particular location the intradermal injection was made, a significant preference again was indicated for the present method.

TABLE 6

| | Preferred injection | | |
| Delivery Method | Deltoid | Volar | Total |
| --- | --- | --- | --- |
| Standard Procedure | 8 | 9 | 17 |
| Present Method | 38 | 52 | 90 |
| No Preference | 0 | 0 | 1 |
| Total | 46 | 61 | 108 |

A visual inspection was made after each intradermal injection to determine the amount of leakage of the saline solution from the injection site. A four point scale was used to rate the amount of leakage. Zero was selected to indicate no leakage and three was selected to indicated a significant amount of leakage. The results indicated there was no statistically discernable difference between the standard procedure and the present method.

TABLE 7

| | Rating | | | |
| Delivery Method | 0 | 1 | 2 | 3 |
| --- | --- | --- | --- | --- |
| Standard Procedure | 142 | 71 | 1 | 0 |
| Present Method | 137 | 68 | 6 | 5 |

A visual inspection was made of each intradermal injection site to determine the level of bleeding that resulted from the injection. The same four point scale used for the leakage evaluation was used to evaluate the level of bleeding. The data shown in Table 8 indicates the present method resulted in less bleeding than the standard procedure did:

TABLE 8

| | Rating | | | |
| Delivery Method | 0 | 1 | 2 | 3 |
| --- | --- | --- | --- | --- |
| Standard Procedure | 98 | 109 | 5 | 2 |
| Present Method | 177 | 38 | 0 | 1 |

After the clinical trial was completed, each of the twelve nurses was surveyed about their overall satisfaction with the present method when compared to the standard procedure. Each of the twelve nurses indicated that it was easy to keep the skin engaging surface 42 against the skin of the subject when administering the intradermal injection. Eight of the nurses indicated the overall performance of the present method was excellent. Three indicated the overall performance was better than acceptable and only one indicated the performance was less than acceptable. Eleven of the twelve nurses indicated a preference for the present method while only one indicated no preference. All twelve of the nurses indicated the present method was easier to perform than the standard procedure. The nurses were evenly split as to the ease in of injecting the saline solution between the two procedures with two nurses having no preference. All twelve nurses indicated the present method proved easier to keep the needle in the proper place. Eleven of the twelve nurses indicated it was preferable to give an intradermal injection at an angle of ninety degrees than fifteen degrees. One nurse had no preference. Seven of the nurses indicated the present method was more effective in delivering a proper injection. Two nurses indicated the standard procedure was more effective, and three nurses indicated no preference.

Accordingly, the method of the present invention may be used to intradermally inject various substance selected from the group consisting of drugs, vaccines and the like used in the prevention, diagnosis, alleviation, treatment, or cure of diseases to expose the injected substance to the microcirculatory blood vasculature and the lymphatic plexuses where the substance can be taken up, absorbed or can interact with the cells to obtain systemic delivery or an immune response in cases where the substance is either a drug or one or more vaccines. In this way, by targeting the dermal space, the immune response, pharmacokinetics (PK) and pharmacodynamics (PD) parameters of the substance can be dramatically altered, which, for example, in the case of improved bioavailability or improved immune response, can result in a reduction in the amount of the necessary dose of the substance to be delivered. These substances may include: (i) drugs such as Alpha-1 anti-trypsin, Anti-Angiogenesis agents, Antisense, butorphanol, Calcitonin and analogs, Ceredase, COX-II inhibitors, dermatological agents, dihydroergotamine, Dopamine agonists and antagonists, Enkephalins and other opioid peptides, Epidermal growth factors, Erythropoietin and analogs, Follicle stimulating hormone, G-CSF, Glucagon, GM-CSF, granisetron, Growth hormone and analogs (including growth hormone releasing hormone), Growth hormone antagonists, Hirudin and Hirudin analogs such as hirulog, IgE suppressors, Insulin, insulinotropin and analogs, Insulin-like growth factors, Interferons, Interleukins, Leutenizing hormone, Leutenizing hormone releasing hormone and analogs, Low molecular weight heparin, M-CSF, metoclopramide, Midazolam, Monoclonal antibodies, Narcotic analgesics, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, Thrombolytics, Tissue plasminogen activators, TNF-, and TNF-antagonists; (ii) vaccines, with or without carriers/adjuvants, such as prophylactics and therapeutic antigens (including but not limited to subunit protein, peptide and polysaccharide, polysaccharide conjugates, toxoids, genetic based vaccines, live attenuated, reassortant, inactivated, whole cells, viral and bacterial vectors) in connection with, addiction, arthritis, cholera, cocaine addiction, diphtheria, tetanus, HIB, Lyme disease, meningococcus, measles, mumps, rubella, varicella, yellow fever, Respiratory syncytial virus, tick borne japanese encephalitis, pneumococcus, streptococcus, typhoid, influenza, hepatitis, including hepatitis A, B, C and E, otitis media, rabies, polio, HIV, parainfluenza, rotavirus, Epstein Barr Virus, CMV, chlamydia, non-typeable haemophilus, moraxella catarrhalis, human papilloma virus, tuberculosis including BCG, gonorrhoea, asthma, atteroschlerosis malaria, E-coli, Alzheimers, H. Pylori, salmonella, diabetes, cancer, herpes simplex, human papilloma; and (iii) other substances in all of the major therapeutics such as Agents for the common cold, Anti-addiction, anti-allergy, anti-emetics, anti-obesity, antiosteoporeteic, anti-infectives, analgesics, anesthetics, anorexics, antiarthritics, antiasthmatic agents, anticonvulsants, anti-depressants, antidiabetic agents, antihistamines, anti-inflammatory agents, antimigraine preparations, antimotion sickness preparations, antinauseants, antineoplastics, antiparkinsonism drugs, antipruritics, antipsychotics, antipyretics, anticholinergics, benzodiazepine antagonists, vasodilators, including general, coronary, peripheral and cerebral, bone stimulating agents, central nervous system stimulants, hormones, hypnotics, immunosuppressives, muscle relaxants, parasympatholytics, parasympathomimetrics, prostaglandins, proteins, peptides, polypeptides and other macromolecules, psychostimulants, sedatives, sexual hypofunction and tranquilizers and major diagnostics such as tuberculin and other hypersensitivity agents.

In addition, it should be appreciated that the substance delivered in accordance with the method of the present invention can be a combination drugs or vaccines, such as for example vaccines against (i) measles, mumps and rubella, (ii) diphtheria, tetanus and acellular pertussis, (iii) hepatitis A and hepatitis B, (iv) haemophilus influenza B, diphtheria, tetanus and acellular pertussis, (v) haemophilus influenza B, hepatitis B, diphtheria, tetanus and acellular pertussis, and (vi) haemophilus influenza B, inactivated polio, diphtheria, tetanus and acellular pertussis which are commonly delivered in combination to the subcutaneous (SQ) and/or intramuscular (IM) space.

During SQ or IM injections with a needle, it is generally recommended practice to expel or purge any air that may be contained within the needle and needle hub prior to the injection. This practice eliminates the risk of accidentally injecting air into a blood vessel sufficient to create an air embolism into the vasculature. For intradermal injections, this risk is eliminated because the depth at which an intradermal injection is given is not in the region of large blood vessels into which a needle can penetrate. Therefore, purging the needle and needle hub of air is not required prior to an intradermal injection. Furthermore, it is anticipated that purposely injecting a small volume of air into the intradermal space just prior to injecting the substance may facilitate the formation of a wheal, which is the indicator of a successful intradermal injection. It is believed that this occurs because during an intradermal injection a reasonably high amount of pressure needs to be generated to separate the dermal layers and open a pathway through which the substance can flow. Air, being a less viscous fluid than a substance such as a drug or vaccine, flows easier into the dermal space, thereby creating a pathway downstream to the drug or vaccine. This sequential delivery of air followed by drug or vaccine is believed to increase the likelihood of a successful intradermal injection.

The present invention also includes the use of the above substances in the preparation of a filled device for making an intradermal injection into the skin of an animal. Accordingly, referring now to FIG. 10, an example of a way of preparing the filled devices designed according to this invention is schematically illustrated in flow chart format. When the device includes a syringe of the style illustrated in FIG. 3, the following basic procedure is useful for preparing prefilling the syringes with a desired substance for such use.

A supply of syringe barrels 200 includes the desired form of syringe, such as those illustrated and discussed above having a first end and a second end. A locally controlled environment 202 preferably is maintained in a known manner. The locally controlled environment 202 preferably is situated to immediately accept the syringes without requiring any intermediate cleaning or sterilizing steps between the supply 200 and the environment 202.

In one example, the syringe barrels are washed with air at 204 to remove any particulates from the syringes. The syringes preferably are then coated at 206 with a lubricant such as a conventional lubricating silicone oil on the inner surface. The lubricant facilitates moving the stopper 70 and plunger rod 66 through the syringe during actual use of the device.

The end of syringes to which the needle assembly 20 will eventually be attached may be capped with a tip cap within the environment 202. In one example, tip caps are supplied at 208. The tip caps are air washed at 210. The cleaned tip caps and syringe barrels are conveyed to an assembly device 212 where the tip caps are secured onto the syringes. The syringe barrel assemblies are then conveyed to a filling station 214 to be filled with the desired substance.

Once filled as desired, the stoppers 70 are inserted into the open end of the syringes at 220. Prior to inserting the stoppers 70, they preferably are assembled with the plunger rods 66 at 222 and lubricated at 224 with a conventional lubricant in a known manner. The assembled, filled syringes preferably are inspected at 226 for defects and discharged from the locally controlled environment.

Where feasible, the syringes typically will be sterilized at 230 and packaged at 232 into individual packages or into bulk packaging depending on the needs of a particular situation. Suitable sterilization techniques are known and will be chosen by those skilled in the art depending on the needs of a particular situation or to accommodate the properties of a given substance. Sterilizing a device designed according to this invention can be completed before or after packaging. Typically, vaccines are not terminally sterilizable, particularly live vaccines.

Variations of the filling steps are within the scope of this invention. For example, the stopper can be inserted first, then fill the syringe, followed by applying a tip cap. Additionally, the device may be filled just prior to making the injection, particularly in situations where the substance to be injected is in a dry or reconstitutable form.

The actual insertion of the desired substance into the syringe body can be accomplished in any of several known manners. Example preparation and filling techniques are disclosed in U.S. Pat. No. 6,164,044 to Profano et al.; U.S. Pat. No. 6,189,292 to Odell et al.; U.S. Pat. No. 5,620,425 to Heffernan et al.; U.S. Pat. No. 5,597,530 to Smith et al.; U.S. Pat. No. 5,573,042 to DeHaen; U.S. Pat. No. 5,531,255 to Vacca; U.S. Pat. No. 5,519,984 to Beussink et al.; U.S. Pat. No. 5,373,684 to Vacca; U.S. Pat. No. 5,256,154 to Liebert et al.; U.S. Pat. No. 5,207,983 to Liebert et al.; and U.S. Pat. No. 4,718,463 to Jurgens, Jr. et al., each of which is incorporated by reference into this specification.

The description given above provides example implementations of this invention. Variations and modifications may become apparent to those skilled in the art that do not necessarily depart from the basis of this invention. The scope of legal protection given to this invention can only be determined by studying the following claims.

What is claimed is:

1. A method of making an intradermal injection into the skin of an animal to obtain systemic delivery or an immune response comprising the steps of:
    providing a drug delivery device including a needle cannula having a forward needle tip and said needle cannula being in fluid communication with a substance contained in said drug delivery device and including a limiter portion surrounding said needle cannula and said limiter portion including a skin engaging surface, with said needle tip of said needle cannula extending from said limiter portion beyond said skin engaging surface a distance equal to approximately 0.5 mm to approximately 3.0 mm and said needle cannula having a fixed angle of orientation relative to a plane of the skin engaging surface of the limiter portion;
    inserting said needle tip into the skin of an animal and engaging the surface of the skin with said skin engaging surface of said limiter portion such that the skin engaging surface of the limiter portion limits penetration of the needle tip into the dermis layer of the skin of the animal; and
    expelling the substance from said drug delivery device through the needle tip into the skin of the animal to expose the injected substance to the microcirculatory blood vasculature and the lymphatic plexuses.

2. A method as set forth in claim 1 wherein said substance is selected from the group consisting of drugs, vaccines and the like used in the prevention, diagnosis, alleviation, treatment, or cure of diseases.

3. A method as set forth in claim 1 wherein said fixed angle of orientation of said needle cannula is further defined as being generally perpendicular to said plane of said skin engaging surface of the limiter portion within about fifteen degrees.

4. A method as set forth in claim 3 wherein said fixed angle of orientation of said needle cannula is further defined as being ninety degrees relative to said plane of the skin engaging surface of the limiter portion within about five degrees.

5. A method as set forth in claim 2 wherein said substance includes a combination of the drugs or vaccines.

6. A method as set forth in claim 5 wherein said substance is selected from a combination of vaccines against (i) measles, mumps and rubella, (ii) diphtheria, tetanus and acellular pertussis, (iii) hepatitis A and hepatitis B, (iv) haemophilus influenza B, diphtheria, tetanus and acellular pertussis, (v) haemophilus influenza B, hepatitis B, diphtheria, tetanus and a cellular pertussis, and (vi) haemophilus influenza B, inactivated polio, diphtheria, tetanus and acellular pertussis which are commonly delivered in combination to the subcutaneous and/or intramuscular space.

7. A method as set forth in claim 1 further including the step of selecting an injection sight on the skin of the animal.

8. A method as set forth in claim 7 further including the step of cleaning the injection sight on the skin of the animal prior to expelling the substance from the drug delivery device into the skin of the animal.

9. A method as set forth in claim 1 further comprising the step of filling the drug delivery device with the substance.

10. A method as set forth in claim 1 further including the step of pressing said skin engaging surface of said limiter portion against the skin of the animal and applying pressure thereby stretching the skin of the animal.

11. A method as set forth in claim 1 further including the step of withdrawing the needle cannula from the skin after injecting the substance.

12. A method as set forth in claim 1 wherein said step of inserting said forward tip into the skin is further defined by inserting said forward tip into the skin to a depth of from approximately 1.0 mm to approximately 2.0 mm.

13. A method as set forth in claim 1 wherein said step of inserting said forward tip into the skin is further defined by inserting said forward tip into the skin to a depth of 1.5 mm±0.2 mm to 0.3 mm.

14. A method as set forth in claim 1 wherein said substance comprises an influenza vaccine.

15. A method as set forth in claim 1 wherein said substance comprises a hepatitis B vaccine.

16. A method as set forth in claim 1 wherein said substance comprises a rabies vaccine.

17. A method as set forth in claim 1 wherein said substance comprises a cancer vaccine.

18. A method as set forth in claim 1 wherein said substance comprises a genetic based vaccine.

19. A method as set forth in claim 1 wherein said substance comprises a tuberculin test substance.

20. A method of making an intradermal injection with a drug delivery device having a limiter with a skin engaging surface limiting the depth a needle cannula can be inserted into the skin of an animal to obtain systemic delivery or an immune response comprising the steps of:
    exposing a forward tip of said needle cannula extending from a limiter beyond a skin engaging surface a distance equal to approximately 0.5 mm to approximately 3.0 mm and said needle cannula having a fixed angle of orientation relative to the skin engaging surface of the limiter;
    inserting said forward tip of the needle cannula into the skin of the animal at until said skin engaging surface contacts the skin of the animal; and
    expelling a substance from said device into the dermis layer of the skin of the animal to expose the injected substance to the microcirculatory blood vasculature and the lymphatic plexuses.

21. A method as set forth in claim 20 wherein said step of inserting said forward tip into the skin of the animal is further defined by inserting said forward tip into the skin at an angle being generally perpendicular to the skin.

22. A method as set forth in claim 20 wherein said step of inserting said forward tip into the skin of the animal is further defined by inserting said forward tip into the skin at an angle of generally ninety degrees to the skin.

23. A method as set forth in claim 20 wherein said fixed angle of orientation relative to said skin engaging surface is further defined as being generally perpendicular within about fifteen degrees.

24. A method as set forth in claim 23 wherein said drug delivery device comprises a syringe having a barrel and a plunger received within said barrel and said plunger being depressable to expel said substance from said delivery device through the forward tip of said needle cannula.

25. A method as set forth in claim 24 wherein said step of expelling the substance from said delivery device is further defined by grasping said hypodermic needle with a first hand and depressing said plunger with an index finger of a second hand.

26. A method as set forth in claim 24 wherein said step of expelling the substance from said delivery device is further defined by grasping said hypodermic needle with a first hand and depressing said plunger on said hypodermic needle with a thumb of a second hand.

27. A method as set forth in claim 24 wherein said step of inserting the said forward tip into the skin of the animal is further defined by pressing the skin of the animal with said limiter.

28. A method as set forth in claim 24 further including the step of attaching a needle assembly to a tip of said barrel of said syringe with said needle assembly including said needle cannula and said limiter.

29. A method as set forth in claim 28 further including the step of exposing the tip of said barrel before attaching said needle assembly thereto by removing a cap from said tip of said barrel.

30. A method as set forth in claim 20 wherein said animal is human.

31. A method as set forth in claim 24 wherein said step of inserting said forward tip of said needle into the skin of the animal is further defined by simultaneously grasping said hypodermic needle with a first hand and pressing said limiter against the skin of the animal thereby stretching the skin of the animal.

32. A method as set forth in claim 31 wherein said step of expelling the substance is further defined by depressing said plunger with an index finger of the first hand.

33. A method as set forth in claim 31 wherein said step of expelling the substance is further defined by depressing said plunger with a thumb of the first hand.

34. A method as set forth in claim 20 further including the step of withdrawing said forward tip of said needle cannula from the skin of the animal after the substance has been injected into the skin of the animal.

35. A method as set forth in claim 20 wherein said step of inserting said forward tip into the skin is further defined by inserting said forward tip into the skin to a depth of from approximately 1.0 mm to approximately 2.0 mm.

36. A method as set forth in claim 35 wherein said step of inserting said forward tip into the skin is further defined by inserting said forward tip into the skin to a depth of 1.5 mm±0.2 mm to 0.3 mm.

37. A method as set forth in claim 20 wherein said step of exposing said forward tip of said needle cannula is further defined by removing a cap from said delivery device.

38. A method as set forth in claim 20 wherein said substance is selected from the group consisting of drugs, vaccines and the like used in the prevention, diagnosis, alleviation, treatment, or cure of disease.

39. A method as set forth in claim 38 wherein said drugs include Alpha-1 anti-trypsin, Anti-Angiogenesis agents, Antisense, butorphanol, Calcitonin and analogs, Ceredase, COX-II inhibitors, dermatological agents, dihydroergotamine, Dopamine agonists and antagonists, Enkephalins and other opioid peptides, Epidermal growth factors, Erythropoietin and analogs, Follicle stimulating hormone, G-CSF, Glucagon, GM-CSF, granisetron, Growth hormone and analogs (including growth hormone releasing hormone), Growth hormone antagonists, Hirudin and Hirudin analogs such as hirulog, IgE suppressors, Insulin, insulinotropin and analogs, Insulin-like growth factors, Interferons, Interleukins, Leutenizing hormone, Leutenizing hormone releasing hormone and analogs, Low molecular weight heparin, M-CSF, metoclopramide, Midazolam, Monoclonal antibodies, Narcotic analgesics, nicotine, Nonsteroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, Thrombolytics, Tissue plasminogen activators, TNF-, and TNF-antagonist, said vaccines, with or without carriers/adjuvants, include prophylactics and therapeutic antigens (including but not limited to subunit protein, peptide and polysaccharide, polysaccharide conjugates, toxoids, genetic based vaccines, live attenuated, reassortant, inactivated, whole cells, viral and bacterial vectors) in connection with, addiction, arthritis, cholera, cocaine addiction, diphtheria, tetanus, HIB, Lyme disease, meningococcus, measles, mumps, rubella, varicella, yellow fever, Respiratory syncytial virus, tick borne japanese encephalitis, pneumococcus, streptococcus, typhoid, influenza, hepatitis, including hepatitis A, B, C and E, otitis media, rabies, polio, HIV, parainfluenza, rotavirus, Epstein Barr Virus, CMV, chlamydia, non-typeable haemophilus, moraxella catarrhalis, human papilloma virus, tuberculosis including BCG, gonorrhoea, asthma, atherosclerosis malaria, E-coli, Alzheimers, H. Pylori, salmonella, diabetes, cancer, herpes simplex, human papilloma and like other substances include all of the major therapeutics such as agents for the common cold, Anti-addiction, anti-allergy, anti-emetics, anti-obesity, antiosteoporeteic, anti-infectives, analgesics, anesthetics, anorexics, antiarthritics, antiasthmatic agents, anticonvulsants, anti-depressants, antidiabetic agents, antihistamines, anti-inflammatory agents, antimigraine preparations, antimotion sickness preparations, antinauseants, antineoplastics, antiparkinsonism drugs, antipruritics, antipsychotics, antipyretics, anticholinergics, benzodiazepine antagonists, vasodilators, including general, coronary, peripheral and cerebral, bone stimulating agents, central nervous system stimulants, hormones, hypnotics, immunosuppressives, muscle relaxants, parasympatholytics, parasympathomimetrics, prostaglandins, proteins, peptides, polypeptides and other macromolecules, psychostimulants, sedatives, sexual hypofunction and tranquilizers and major diagnostics such as tuberculin and other hypersensitivity agents.

40. A method as set forth in claim 38 wherein said substance comprises an influenza vaccine.

41. A method as set forth in claim 38 wherein said substance comprises a hepatitis B vaccine.

42. A method as set forth in claim 38 wherein said substance comprises a rabies vaccine.

43. A method as set forth in claim 38 wherein said substance comprises a cancer vaccine.

44. A method as set forth in claim 38 wherein said substance comprises a genetic based vaccine.

45. A method as set forth in claim 20 wherein said step of expelling the substance from said device into the dermis layer of the skin includes expelling a small volume of air from the device into the dermis layer before expelling said substance.

46. A method of making an intradermal injection into the skin of an animal comprising the steps of:

providing a drug delivery device with a prefillable container including a needle cannula having a forward needle tip and said needle cannula being in fluid communication with a substance contained in said prefillable container and including a limiter portion surrounding said needle cannula and said limiter portion including a skin engaging surface, with said needle tip of said needle cannula extending from said limiter portion beyond said skin engaging surface and said needle cannula having a fixed angle of orientation relative to a plane of the skin engaging surface of the limiter portion;

inserting said needle tip into the skin of an animal and engaging the surface of the skin with said skin engaging surface of said limiter portion such that the skin engaging surface of the limiter portion limits penetration of the needle tip into the dermis layer of the skin of the animal; and expelling a small volume of air and the substance from said drug delivery device through the needle tip into the skin of the animal to expose the injected substance to the microcirculatory blood vascularity and the lymphatic plexuses where the substance can be taken up, absorbed or can interact with the cells to obtain systemic delivery or an immune response in cases where the substance is either a drug or one or more vaccines.

47. A method as set forth in claim 46 wherein said step of inserting said forward tip into the skin of the animal is further defined by inserting said forward tip into the skin at an angle being generally perpendicular to the skin within about fifteen degrees.

48. A method as set forth in claim 47 wherein said step of inserting said forward tip into the skin of the animal is further defined by inserting said forward tip into the skin at an angle of generally ninety degrees to the skin within about five degrees.

49. A method as set forth in claim 46 wherein said limiter portion has a generally flat skin engaging surface surrounding said needle tip having an outside diameter of at least 5 mm.

50. A method as set forth in claim 49 wherein said step of providing a limiter portion is further defined by said forward tip of said needle cannula extending beyond said skin engaging surface a distance equal to approximately 0.5 mm to approximately 3.0 mm.

51. A method as set forth in claim 46 wherein said barrel of said syringe is made of glass.

52. A method as set forth in claim 46 wherein said step of inserting said forward tip into the skin is further defined by inserting said forward tip into the skin to a depth of from approximately 1.0 mm to approximately 2.0 mm.

53. A method as set forth in claim 46 wherein said step of inserting said forward tip into the skin is further defined by inserting said forward tip into the skin to a depth of 1.5 mm±0.2 mm to 0.3 mm.

54. A method as set forth in claim 46 wherein said substance is selected from the group consisting of drugs, vaccines and the like used in the prevention, diagnosis, alleviation, treatment, or cure of diseases.

55. A method as set forth in claim 46 wherein said substance is selected from the group consisting of drugs, vaccines and the like used in the prevention, diagnosis, alleviation, treatment, or cure of diseases.

56. A method as set forth in claim 55 wherein said substances includes a combination of drugs or vaccines.

57. A method as set forth in claim 56 wherein said substance is selected from vaccine combinations against (i) measles, mumps and rubella, (ii) diphtheria, tetanus and acellular pertussis, (iii) hepatitis A and hepatitis B, (iv) haemophilus influenza B, diphtheria, tetanus and acellular pertussis, (v) haemophilus influenza B, hepatitis B, diphtheria, tetanus and acellular pertussis, and (vi) haemophilus influenza B, inactivated polio, diphtheria, tetanus and acellular pertussis which are commonly delivered in combination to the subcutaneous and/or intramuscular space.

\* \* \* \* \*